US007762811B2

(12) United States Patent
Takabatake (10) Patent No.: US 7,762,811 B2
(45) Date of Patent: Jul. 27, 2010

(54) ORTHODONTICS ASSISTING SYSTEM AND INDEX MEMBER AND ARRANGING DEVICE FOR USE THEREIN

(75) Inventor: Ichiro Takabatake, Tokyo (JP)

(73) Assignee: Japan Dental Support Co. Ltd., Tokyo (JP)

(*) Notice: Subject to any disclaimer, the term of this patent is extended or adjusted under 35 U.S.C. 154(b) by 223 days.

(21) Appl. No.: 11/886,152

(22) PCT Filed: Mar. 3, 2006

(86) PCT No.: PCT/JP2006/304166

§ 371 (c)(1),
(2), (4) Date: Sep. 12, 2007

(87) PCT Pub. No.: WO2006/098174

PCT Pub. Date: Sep. 21, 2006

(65) Prior Publication Data

US 2008/0268399 A1    Oct. 30, 2008

(30) Foreign Application Priority Data

Mar. 16, 2005    (JP)    ............................. 2005-076109

(51) Int. Cl.
*A61C 19/04* (2006.01)
(52) U.S. Cl. .................. 433/68; 433/3; 433/24
(58) Field of Classification Search .................. 433/24, 433/60, 72, 75, 213, 68; 600/589, 590
See application file for complete search history.

(56) References Cited

U.S. PATENT DOCUMENTS 5,685,879 A * 11/1997 Phillips .................... 606/86 R
5,975,893 A * 11/1999 Chishti et al. .................. 433/6
7,156,661 B2 * 1/2007 Choi et al. .................. 433/213
2006/0127836 A1 * 6/2006 Wen ............................ 433/24

FOREIGN PATENT DOCUMENTS

| JP | 2002-514125 | 5/2002 |
| JP | 2003-33341 | 4/2003 |
| WO | WO 98/58596 | 12/1998 |
| WO | 03/068099 | 8/2003 |

OTHER PUBLICATIONS

International Search Report mailed May 23, 2006 (English and Japanese text).

* cited by examiner

*Primary Examiner*—Cris L Rodriguez
*Assistant Examiner*—Eric Rosen
(74) *Attorney, Agent, or Firm*—Nixon & Vanderhye P.C.

(57) ABSTRACT

An orthodontics assisting system includes index members which indicate respective reference positions of a pre-correction dentition model and a post-correction predictive dentition model; an arranging device 6 for arranging the index members; an image data generating means for generating image data by imaging the pre-correction dentition model and the post-correction predictive dentition model; a screen display means for screen-displaying a pre-correction dentition image and a post-correction predictive dentition image respectively based on the image data; a position adjusting means for adjusting mutual display positions of the pre-correction dentition image and the post-correction predictive dentition image; and a tooth position adjusting means for adjusting the display position of a teeth image.

10 Claims, 7 Drawing Sheets

ORTHODONTICS ASSISTING SYSTEM AND INDEX MEMBER AND ARRANGING DEVICE FOR USE THEREIN

This application is the U.S. national phase of International Application No. PCT/JP2006/304166 filed 3 Mar. 2006 which designated the U.S. and claims priority to JP 2005-076109 filed 16 Mar. 2005, the entire contents of each of which are hereby incorporated by reference.

TECHNICAL FIELD

The present invention relates to an orthodontics assisting system for assisting phased correction planning and the like of orthodontics by adjusting the display position of a teeth image included in a two-dimensional or three-dimensional dentition image which is displayed on a screen, as well as an index member and an arranging device for use therein.

BACKGROUND ART

[Patent Document 1] JP-A-2004-267790

In patent document 1, for example, an orthodontics assisting system is proposed in which a plaster-made pre-correction dentition model fabricated by taking an impression from a patient's teeth before orthodontics is imaged by using a scanner such as a laser scanner to generate pre-correction dentition image data, a pre-correction dentition image based on the generated pre-correction dentition image data is presented so as to be visible by using a computer (including a CPU, a memory, a monitor, etc.), and a presumptive post-correction predictive dentition image after orthodontics is created by rearranging on the computer individual tooth images included in the presented pre-correction dentition image while referring to a prescription and the like prepared by a dentist. The three-dimensional images created by such an orthodontics assisting system are used in such as the phased correction planning of orthodontics and the fabrication of orthodontic mouthpieces.

DISCLOSURE OF THE INVENTION

Problems that the Invention is to Solve

Incidentally, in such an orthodontics assisting system, since images of teeth included in the pre-correction dentition image are rearranged on the computer to create a post-correction predictive dentition image, the images of teeth included in the post-correction predictive dentition image are arranged respectively on the basis of only the pre-correction dentition image on the computer, with the result that it is difficult to accurately create a desired post-correction predictive dentition image. In addition, even if a pre-correction dentition model before orthodontics and a post-correction predictive dentition model after orthodontics are respectively fabricated and are imaged to generate a pre-correction dentition image and a post-correction predictive dentition image, the mutual positioning of the pre-correction dentition image and the post-correction predictive dentition image is difficult.

The present invention has been devised in view of the above-described aspects, and its object is to provide an orthodontics assisting system which makes it possible to accurately create a desired post-correction predictive dentition image, and makes it possible to simply and accurately perform the mutual positioning of the pre-correction dentition image and the post-correction predictive dentition image, as well as an index member and an arranging device for use therein.

Means for Solving the Problems

An orthodontics assisting system in accordance with the invention comprises: index members which indicate respective reference positions of a pre-correction dentition model having a dentition shape before orthodontics and a post-correction predictive dentition model having a predictive dentition shape after orthodontics; an arranging device for arranging said index members on the pre-correction dentition model and the post-correction predictive dentition model, respectively, to cause said index members to indicate the reference positions, respectively; image data generating means for generating pre-correction dentition image data including first index image data based on said index member arranged on the pre-correction dentition model and post-correction predictive dentition image data including second index image data based on said index member arranged on the post-correction predictive dentition model, by imaging the pre-correction dentition model and the post-correction predictive dentition model, respectively, with said index members respectively arranged thereon by said arranging device; screen display means for screen-displaying a pre-correction dentition image and a post-correction predictive dentition image respectively based on the pre-correction dentition image data and the post-correction predictive dentition image data generated by said image data generating means; position adjusting means for adjusting on the basis of the first and second index image data mutual display positions of the pre-correction dentition image and the post-correction predictive dentition image which are screen-displayed by said screen display means; and tooth position adjusting means for extracting teeth image data from the pre-correction dentition image data and for adjusting display positions with respect to the post-correction predictive dentition image of teeth images based on the extracted teeth image data.

According to the orthodontics assisting system in accordance with the invention, the orthodontics assisting system is comprised of the index members which indicate respective reference positions of the pre-correction dentition model having a dentition shape before orthodontics and the post-correction predictive dentition model having a predictive dentition shape after orthodontics; the arranging device for arranging the index members on the pre-correction dentition model and the post-correction predictive dentition model, respectively, to cause the index members to indicate the reference positions, respectively; the image data generating means for generating the pre-correction dentition image data including the first index image data based on the index member arranged on the pre-correction dentition model and the post-correction predictive dentition image data including the second index image data based on the index member arranged on the post-correction predictive dentition model, by imaging the pre-correction dentition model and the post-correction predictive dentition model, respectively, with the index members respectively arranged thereon by the arranging device; the screen display means for screen-displaying the pre-correction dentition image and the post-correction predictive dentition image respectively based on the pre-correction dentition image data and the post-correction predictive dentition image data generated by the image data generating means; the position adjusting means for adjusting on the basis of the first and second index image data the mutual display positions of the pre-correction dentition image and the post-correction predictive dentition image which are screen-displayed by the screen display means; and the tooth position adjusting means for extracting the teeth image data from the pre-correction dentition image data and for adjusting display positions with respect to the post-correction predictive dentition image of teeth images based on the extracted teeth image data. Therefore, it is possible to accurately create a desired post-correction predictive dentition image on the basis of the post-correction predictive dentition model. Moreover, the mutual positioning of the pre-correction dentition image and the post-correction predictive dentition image can be performed simply and accurately on the basis of the first and second index image data.

In a preferred example of the orthodontics assisting system in accordance with the invention, the index member has a plate-like body and a projection provided on the plate-like body, and, more preferably, the projection of such an index member is semispherical. According to such preferred examples, since the index members are respectively provided on the pre-correction dentition model and the post-correction predictive dentition model, in a case where the pre-correction dentition model and the post-correction predictive dentition model are imaged as image data for use in a computer or the like, the first index image data which clearly indicates the reference position of the pre-correction dentition image based on the post-correction predictive dentition model and the second index image data which clearly indicates the reference position of the post-correction predictive dentition image based on the post-correction predictive dentition model can be obtained on the basis of the respective imaged index members. Hence, the mutual positioning of the display positions of the pre-correction dentition image based on the pre-correction dentition model and the post-correction predictive dentition image based on the post-correction predictive dentition model can be performed simply and accurately.

In another preferred example of the orthodontics assisting system in accordance with the invention, the arranging device includes holding means for holding the index members; supporting means which supports the holding means and is mounted on each of the model teeth of the pre-correction dentition model and the post-correction predictive dentition model; and a position adjusting mechanism for adjusting the position of the holding means with respect to each of the pre-correction dentition model and the post-correction predictive dentition model. According to such a preferred example, particularly since the supporting means is mounted on the model teeth, the index members can be accurately disposed at arbitrary reference positions with respect to the pre-correction dentition model and the post-correction predictive dentition model. Moreover, by similarly adjusting the position of the holding means with respect to each of the pre-correction dentition model and the post-correction predictive dentition model by the position adjusting mechanism, the position of the index member with respect to the pre-correction dentition model and the position of the index member with respect to the post-correction predictive dentition model can be made to accurately coincide with each other. Thus, the mutual display positions of the pre-correction dentition image and the post-correction predictive dentition image can be made to more accurately coincide with each other.

In still another preferred example of the orthodontics assisting system in accordance with the invention, the supporting means includes a plurality of upright pins each having a tip and each adapted at the tip to be abutted against a depression in an occlusal surface of the respective model tooth so as to be erected uprightly on that respective model tooth. According to such a preferred example, the supporting means can be mounted simply and accurately on the respective model teeth of the pre-correction dentition model and the post-correction predictive dentition model.

In a further preferred example of the orthodontics assisting system in accordance with the invention, the orthodontics assisting system further comprises: storage means for storing the pre-correction dentition image data, the post-correction predictive dentition image data, the teeth image data, and data showing results of respective position adjustment by the position adjusting means and the tooth position adjusting means, respectively. According to such a preferred example, if the above-described various data are once created by the orthodontics assisting system, those various data can be referred to in an ex-post manner. Thus, it is possible to suitably assist the phased correction planning of orthodontics and the fabrication of orthodontic mouthpieces having various shapes corresponding to such phased correction planning.

ADVANTAGES OF THE INVENTION

According to the invention, it is possible to provide an orthodontics assisting system which makes it possible to accurately create a desired post-correction predictive dentition image, and makes it possible to simply and accurately perform the mutual positioning of the pre-correction dentition image and the post-correction predictive dentition image, as well as an index member and an arranging device for use therein.

Next, a more detailed description will be given of an example of the mode for carrying out the invention on the basis of an embodiment illustrated in the drawings. It should be noted that the present invention is not limited to the embodiment.

BRIEF DESCRIPTION OF THE DRAWINGS

FIG. 11(a) is an explanatory plan view of another index member in the embodiment shown in FIG. 1; and FIG. 11(*b*) is an explanatory plan view of still another index member in the embodiment shown in FIG. 1

BEST MODE FOR CARRYING OUT THE INVENTION

Figure 5:
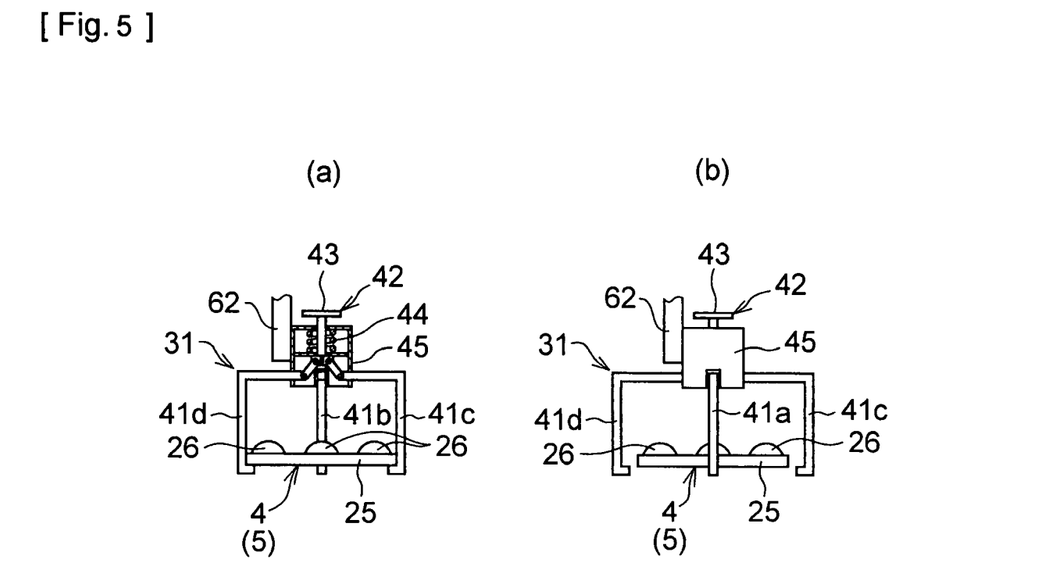
FIGS. 5(a) and 5(b) are explanatory diagrams of mainly a holding means and an index member in the embodiment shown in FIG. 1.
Figure 6:
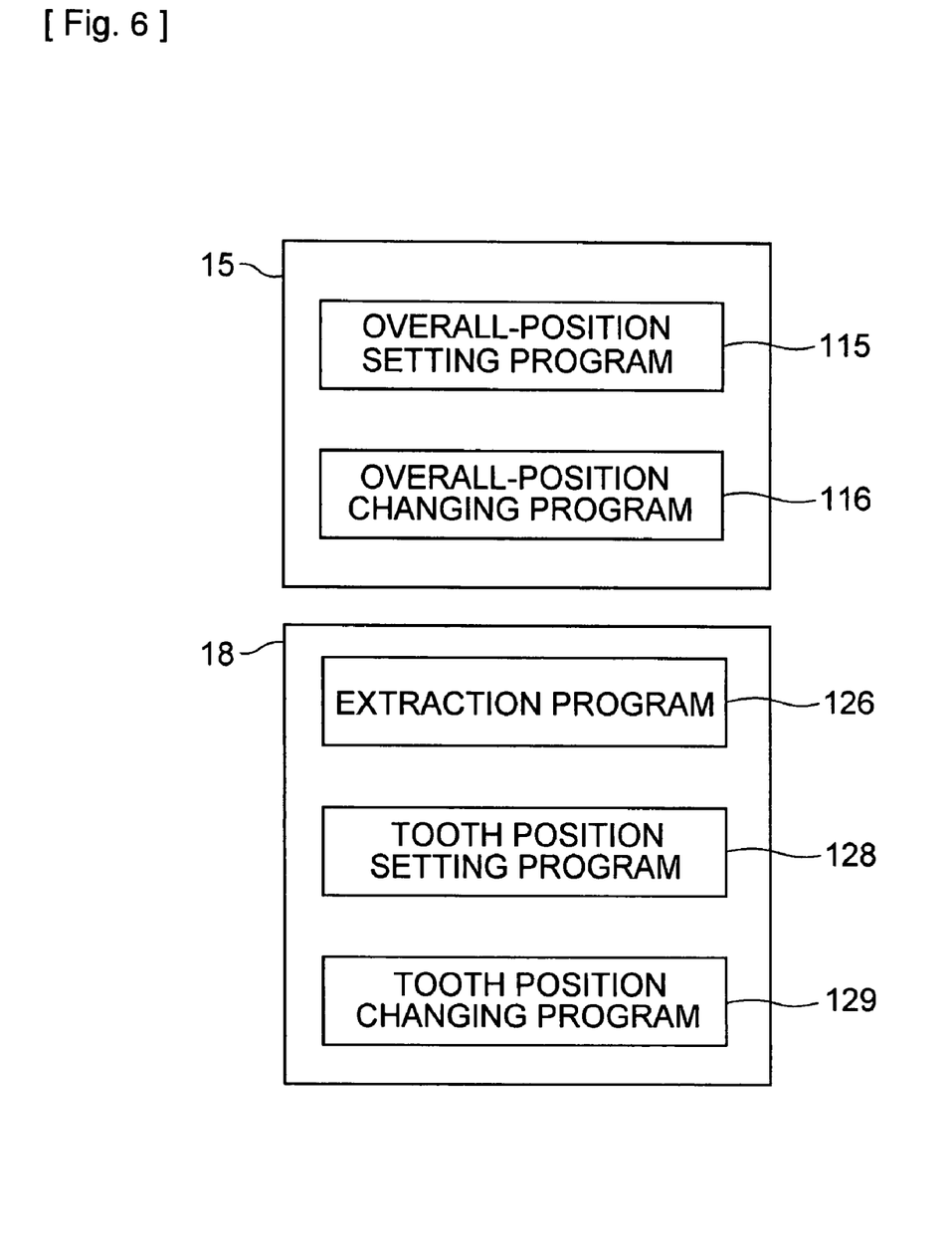
FIG. 6 is an explanatory conceptual diagram concerning programs stored mainly in a storage means in the embodiment shown in FIG. 1.
Figure 7:
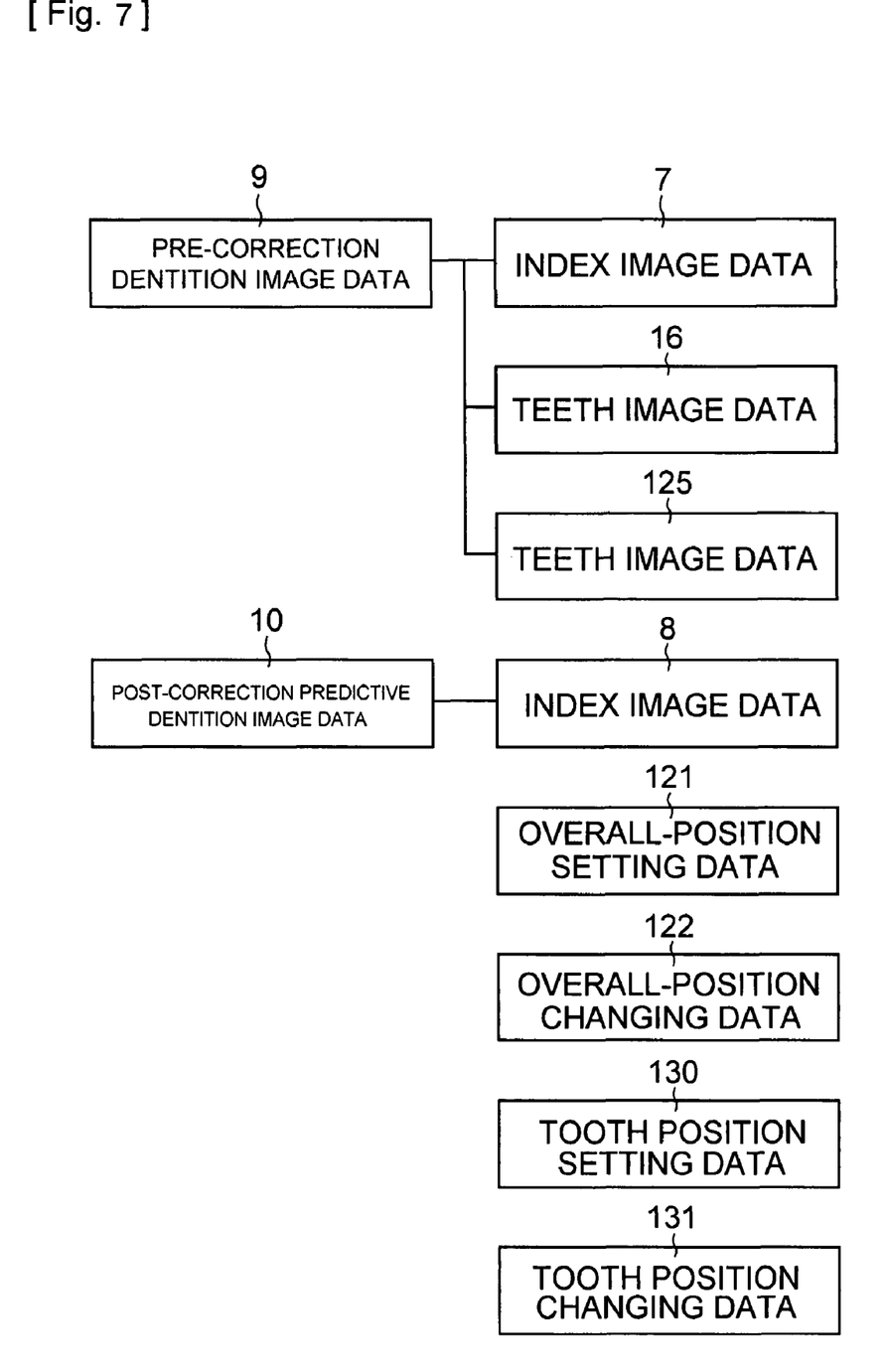
FIG. 7 is an explanatory conceptual diagram concerning data stored mainly in the storage means in the embodiment shown in FIG. 1.
Figure 8:
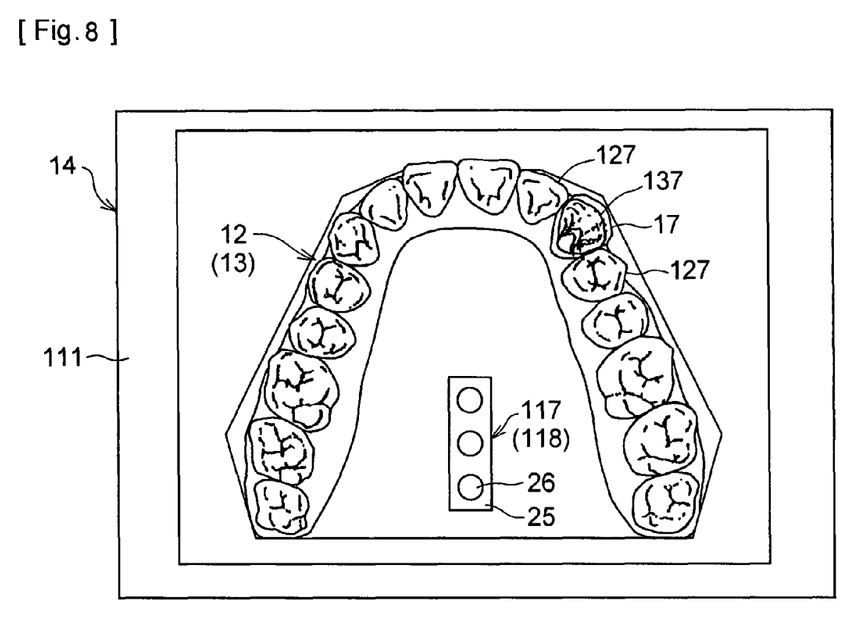
FIG. 8 is an explanatory diagram concerning a screen display of a dentition image by mainly a screen display means in the embodiment shown in FIG. 1.
Figure 9:
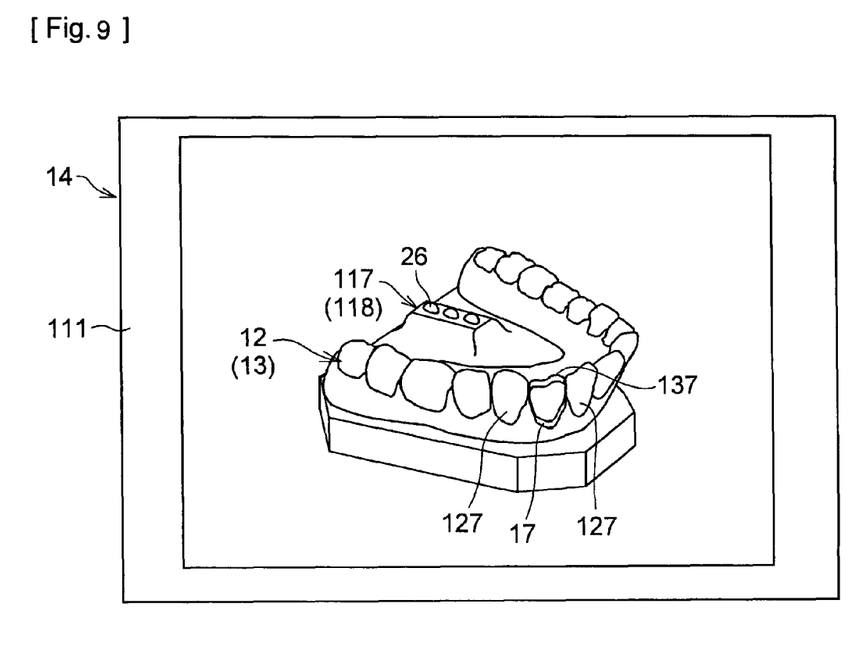
FIG. 9 is an explanatory diagram concerning a screen display of a dentition image by mainly the screen display means in the embodiment shown in FIG. 1.
Figure 10:
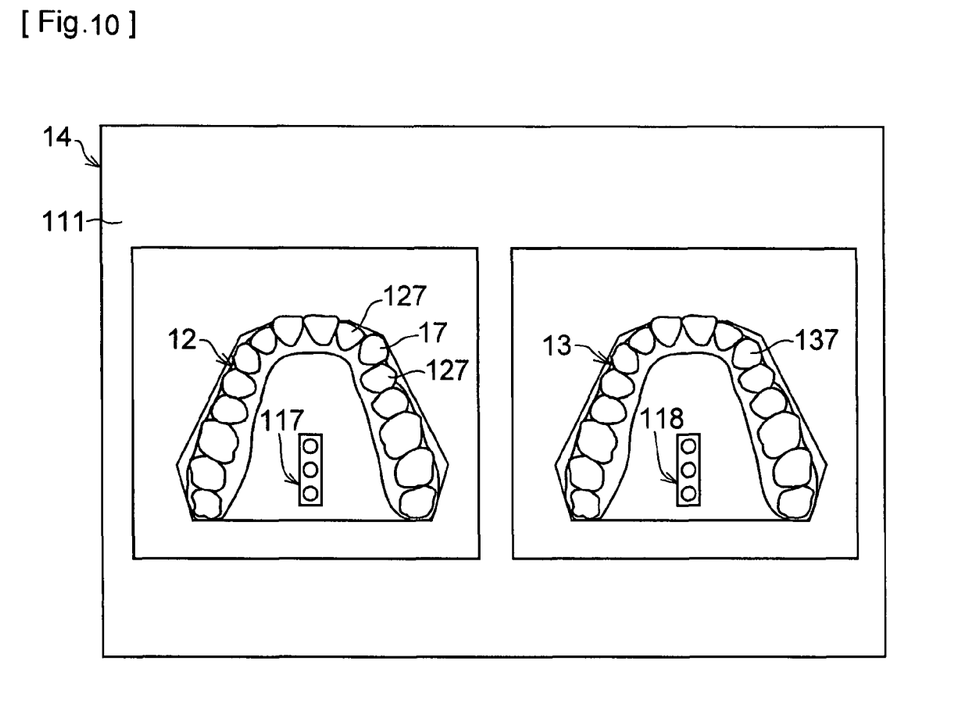
FIG. 10 is an explanatory diagram concerning a screen display of a dentition image by mainly another screen display means in the embodiment shown in FIG. 1.

In FIGS. 1 to 10, an orthodontics assisting system 1 in accordance with this embodiment is comprised of index members 4 and 5 which indicate respective overall reference positions of a pre-correction dentition model 2 having a dentition shape before orthodontics and a post-correction predictive dentition model 3 having a predictive dentition shape after orthodontics; an arranging device 6 for arranging the index members 4 and 5 on the pre-correction dentition model 2 and the post-correction predictive dentition model 3, respectively, to cause the index members 4 and 5 to indicate the reference positions, respectively; an image data generating means 11 for generating pre-correction dentition image data 9 including index image data 7 shown in FIG. 7 and based on the index member 4 arranged on the pre-correction dentition model 2 and post-correction predictive dentition image data 10 including index image data 8 shown in FIG. 7 and based on the index member 5 arranged on the post-correction predictive dentition model 3, by imaging the pre-correction dentition model 2 and the post-correction predictive dentition model 3, respectively, with the index members 4 and 5 respectively arranged thereon by the arranging device 6; a screen display means 14 for screen-displaying a pre-correction dentition image 12 and a post-correction predictive dentition image 13 shown in FIGS. 8 to 10 and respectively based on the pre-correction dentition image data 9 and the post-correction predictive dentition image data 10 generated by the image data generating means 11; an overall-position adjusting means 15 for adjusting on the basis of the index image data 7 and 8 mutual overall display positions of the pre-correction dentition image 12 and the post-correction predictive dentition image 13 which are screen-displayed by the screen display means 14; a tooth position adjusting means 18 for extracting teeth image data 16 and 125 from the pre-correction dentition image data 9 and for adjusting display positions with respect to the post-correction predictive dentition image 13 of teeth images 17 and 127 based on the extracted teeth image data 16 and 125; and a storage means 19 for storing the pre-correction dentition image data 9, the post-correction predictive dentition image data 10, and the teeth image data 16 and 125, as well as data showing the results of respective position adjustment by the overall-position adjusting means 15 and the tooth position adjusting means 18, respectively.

The pre-correction dentition model 2 is fabricated by making an impression from a patient's teeth before orthodontics and may be a plaster cast or the like. In the post-correction predictive dentition model 3, model teeth 21 juxtaposed along the same tooth arrangement as that of the pre-correction dentition model 2 are respectively cut off from each other, and the mutually cut-off model teeth 21 are respectively connected again by means of a thermosoftening (thermoplastic) model gingiva 22 formed of wax or the like. The post-correction predictive dentition model 3 is adapted so as to be able to adjust the position of each of the model teeth 21 by softening the model gingiva 22 on heating. The pre-correction dentition model 2 and the post-correction predictive dentition model 3 are provided on a base 20. As the positions of the model teeth 21 are adjusted, the post-correction predictive dentition model 3 has a presumptive predictive dentition shape in which the dentition shape after final orthodontics is predicted. It should be noted that the post-correction predictive dentition model 3 can be used as a basic mold in the fabrication of such as an orthodontic mouthpiece. In addition, the post-correction predictive dentition model 3 means a dentition model in a state in which it has a predictive dentition shape after orthodontics, and also means a dentition model for adjustment of the positions of the model teeth 21 for assuming the aforementioned predictive dentition shape and which has the same dentition shape as that of the pre-correction dentition model 2. However, when the post-correction predictive dentition model 3 is imaged by the image data generating means 11, the post-correction predictive dentition model 3 is set in a state in which it has a predictive dentition shape after orthodontics.

Since the index members 4 and 5 are formed in a mutually similar fashion, a detailed description will be given hereafter of the index member 4, the same reference numerals will be allotted, as required, to the index member 5 in the drawings, and a detailed description thereof will be omitted.

Figure 1:
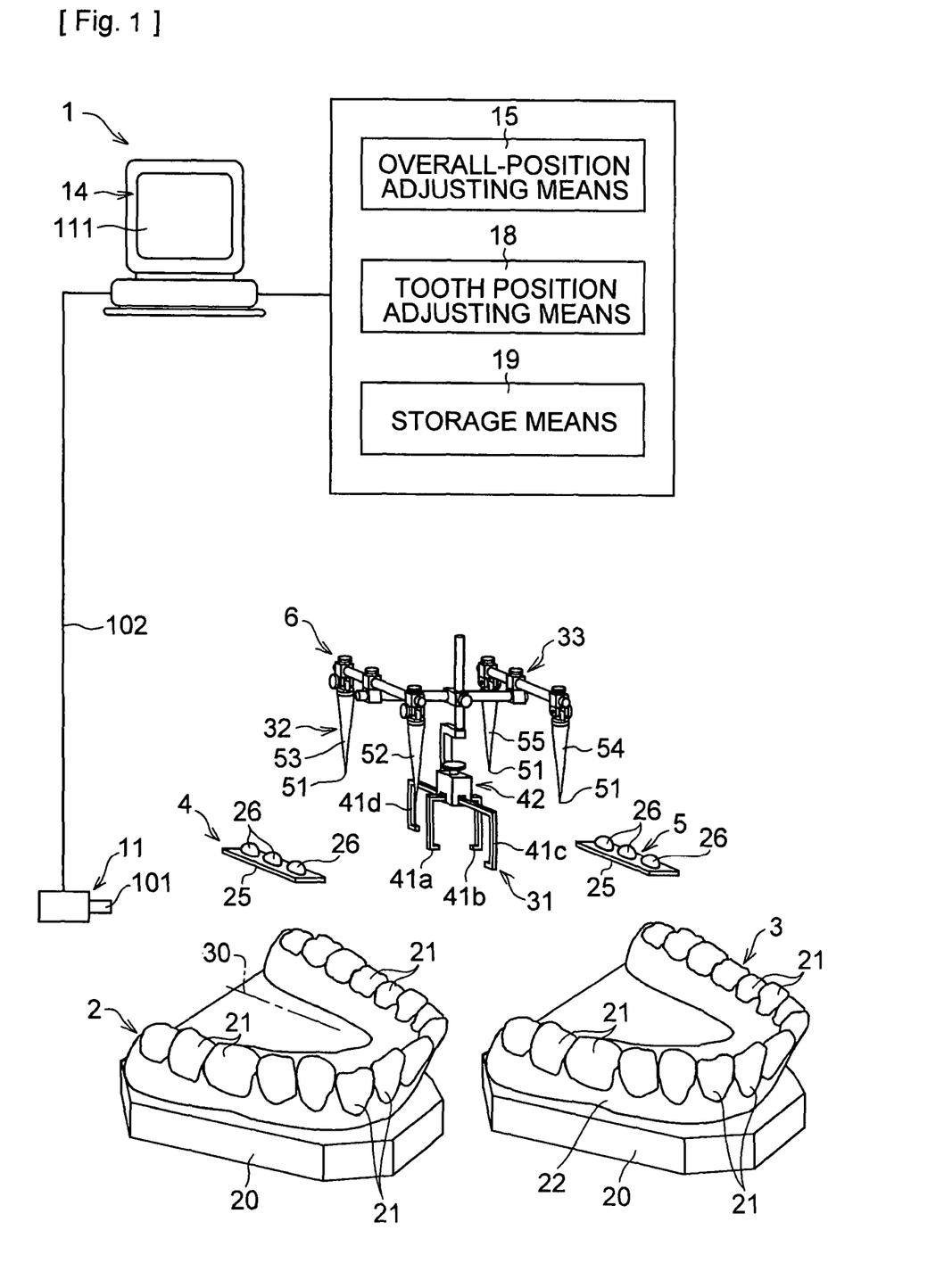
FIG. 1 is an explanatory conceptual diagram of an embodiment of the invention.
Figure 2:
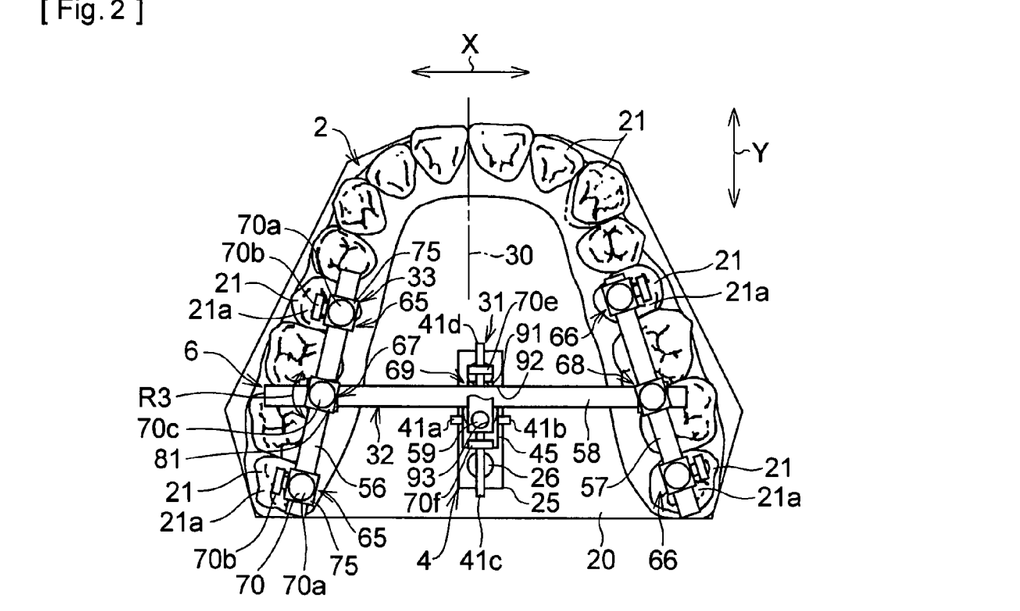
FIG. 2 is an explanatory plan view of mainly an arranging device in the embodiment shown in FIG. 1.
Figure 3:
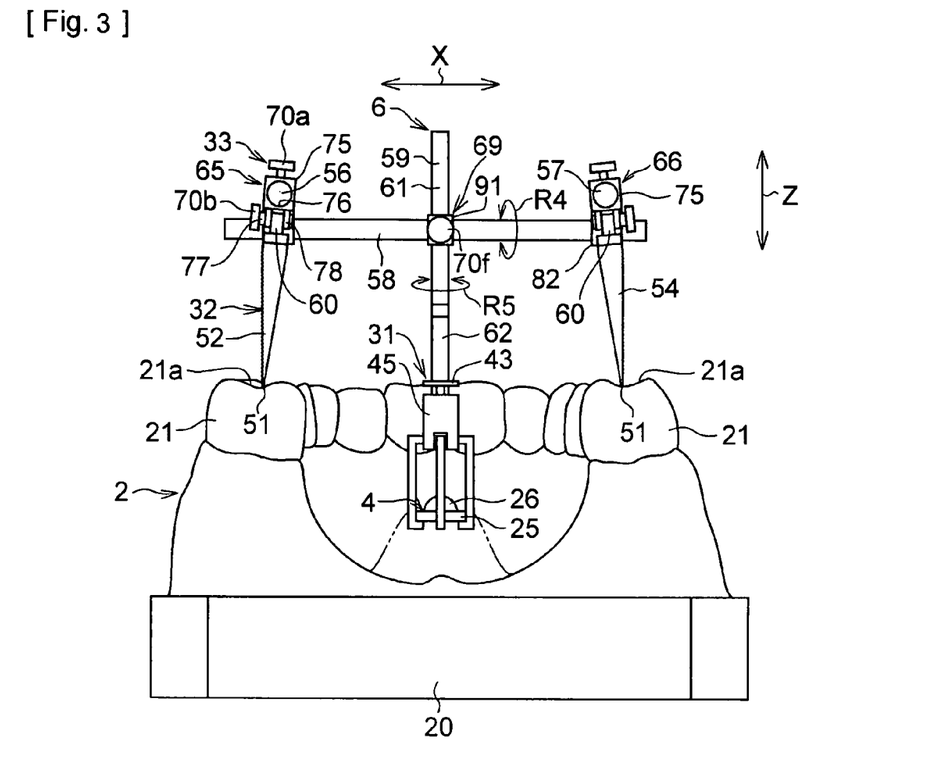
FIG. 3 is an explanatory front elevational view of mainly the arranging device in the embodiment shown in FIG. 1.

As particularly shown in FIGS. 1 to 3 and in FIGS. 5(*a*) and 5(*b*), the index member 4 has a rectangular plate-like body 25 which is fixed to the pre-correction dentition model 2 and three semispherical projections 26 provided integrally on the plate-like body 25 by being aligned in a row in a longitudinal direction of the plate-like body 25. As for the projections 26, three projections are provided in this embodiment, but one, two, or four or more projections may be used, and in the case where the plurality of projections 26 are provided on the plate-like body 25, such projections 26 may be arranged in two or more rows, or may be arranged in rows in such a manner as to form a houndstooth check. In addition, the projection 26 is preferably such that all or a portion of that projection 26 has a semispherical shape (including a semielliptical shape in its longitudinal cross section, an elliptical shape in its transverse cross section, etc.), but it is sufficient if the projection 26 projects from the plate-like body 25. For example, the projection 26 may have a cylindrical shape (including an elliptical shape in its cross section etc.); a prismatic shape (including a triangular prismatic shape, a quadrangular prismatic shape (including a cubic shape and a rectangular parallelepiped shape), a polygonal prismatic shape, etc.); a hollow cylindrical shape (including a hollow elliptical shape in its cross section); a square tubular shape (including a hollow cubic shape, a hollow rectangular parallelepiped shape, a hollow polyhedral shape, etc.); a conical shape (including an elliptical shape in its cross section etc.); a pyramidal shape (including a triangular pyramidal shape, a rectangular pyramidal shape, a polygonal pyramidal shape, etc.); a truncated conical shape (including an elliptical shape in its cross section etc.); and a truncated pyramidal shape (including a truncated triangular pyramidal shape, a truncated rectangular pyramidal shape, a truncated polygonal pyramidal shape, etc.). Such an index member 4, when arranged on the pre-correction dentition model 2 by the arranging device 6, functions as a member for indicating an overall reference position of the pre-correction dentition model 2. It should be noted that the reference position of the pre-correction dentition model 2 in its entirety is arbitrarily set by an operator of the arranging device 6 and may be set on, for instance, a median line 30 of the pre-correction dentition model 2.

As shown in FIG. 1 to FIGS. 5(*a*) and 5(*b*), the arranging device 6 includes a holding means 31 for holding the index members 4 and 5; a supporting means 32 which supports the holding means 31 and is mounted on each of the model teeth 21 of the pre-correction dentition model 2 and the post-correction predictive dentition model 3; and a position adjusting mechanism 33 for adjusting the position of the holding means 31 with respect to each of the pre-correction dentition model 2 and the post-correction predictive dentition model 3.

As particularly shown in FIGS. 1 to 3 and FIGS. 5(a) and 5(b), the holding means 31 has four grip arms 41a, 41b, 41c, and 41d arranged in a cruciform shape so as to be able to grip the plate-like body 25 in cooperation with each other, as well as an approaching and moving-away mechanism 42 connected to each of the grip arms 41a, 41b, 41c, and 41d so as to cause the grip arms 41a, 41b, 41c, and 41d to approach and move away from each other. The arrangement provided is such that the plate-like body 25 is gripped and held by causing the grip arms 41a, 41b, 41c, and 41d to approach each other by the approaching and moving-away mechanism 42, as shown in FIG. 5(a), while the state of holding the plate-like body 25 is released by causing the grip arms 41a, 41b, 41c, and 41d to move away from each other thereby, as shown in FIG. 5(b). It should be noted that the holding means 31 may have, for example, three grip arms (not shown) arranged in a T-shape instead of the grip arms 41a, 41b, 41c, and 41d, such that the plate-like body 25 is gripped and held by causing the three grip arms to approach each other by the approaching and moving-away mechanism 42, while the state of holding the plate-like body 25 is released by causing the three grip arms to move away from each other thereby.

The grip arms 41a and 41b, which are opposed to each other in an X direction, are respectively formed in a mutually similar manner. The grip arms 41c and 41d, which are opposed to each other in a Y direction perpendicular to the X direction, are respectively formed in a mutually similar manner. An elastic body (not shown) formed of rubber (including natural rubber and synthetic rubber such as silicone rubber) or the like is fitted to that portion of each of the grip arms 41a, 41b, 41c, and 41d which abuts against the index members 4 and 5.

The approaching and moving-away mechanism 42 includes a grip operation member 43 connected to an end of each of the grip arms 41a, 41b, 41c, and 41d so as to cause the grip arms 41a and 41b to approach and move away from each other in the X direction and cause the grip arms 41c and 41d to approach and move away from each other in the Y direction through their movement in a Z direction perpendicular to the X direction and the Y direction; an urging member 44 constituted by a coil spring or the like for urging the grip operation member 43 so as to cause the respective grip arms 41a, 41b, 41c, and 41d to approach each other; and a housing 45 for accommodating the grip operation member 43 and the urging member 44. It should be noted that one end of the grip operation member 43 projects from an upper surface of the housing 45.

The above-described holding means 31 is adapted so that as the grip operation member 43 is operated against the urging force by the urging member 44 in the Z direction, the grip arms 41a, 41b, 41c, and 41d are respectively moved away from each other, and as the grip arms 41a, 41b, 41c, and 41d are caused to approach each other by releasing the operation of the grip operation member 43 against the urging force by the urging member 44, the index member 4 or 5 disposed between the respectively mutually moved-away grip arms 41a and 41b and between the grip arms 41c and 41d is gripped. The index member 4 or 5 is adapted to be held by being thus gripped.

The supporting means 32 includes upright pins 52 and 53 each having a pointed distal end (hereafter referred to as a tip) 51 which is abutted against the model tooth 21 of the pre-correction dentition model 2 or the post-correction predictive dentition model 3 on one side of the median line 30 so as to be erected uprightly on that respective model tooth 21; upright pins 54 and 55 each having a tip 51 which is abutted against the model tooth 21 of the pre-correction dentition model 2 or the post-correction predictive dentition model 3 on the other side of the median line 30 so as to be erected uprightly on that respective model tooth 21; a bridging arm 56 for bridging the upright pins 52 and 53, respectively; a bridging arm 57 for bridging the upright pins 54 and 55, respectively; an X-direction shaft 58 which is disposed between the upright pins 52 and 53 and between the upright pins 54 and 55 and is connected to the bridging arms 56 and 57 in such a manner as to extend in the X direction; and a Z-direction shaft 59 which is disposed between the bridging arms 56 and 57 and is connected to the X-direction axis 58 in such a manner as to extend in the Z direction. The housing 45 of the holding means 31 is fitted to a lower end portion of the Z-direction shaft 59. Each of the upright pins 52 to 55 can be easily erected uprightly on the model tooth 21 by causing its tip 51 to abut against a depression of an occlusal surface 21a of the model tooth 21. It should be noted that the supporting means 32 may have, in substitution for at least one of the upright pins 52, 53, 54, and 55, an upright pin (not shown) in which an impression portion for taking an impression of the occlusal surface 21a of the model tooth 21 of the pre-correction dentition model 2 or the post-correction predictive dentition model 3 is provided at its tip. According to such an upright pin, the arranging device 6 can be mounted accurately and simply on the model tooth 21 by bringing the impression portion of a shape complementary to the occlusal surface 21a into surface contact with that occlusal surface 21a. The aforementioned impression portion may be formed from a material such as silicone, rubber, clay, compound, alginate, wax, plaster, or the like.

A connecting portion 60, which is connected to a pin connector 65 so as to be rotatable in an R2 direction, is provided on an upper end of each of the upright pins 52 and 53. A connecting portion 60, which is connected to a pin connector 66 so as to be rotatable in the R2 direction, is similarly provided on an upper end of each of the upright pins 54 and 55 in the same way as the upright pins 52 and 53. The bridging arms 56 and 57 and the X-direction shaft 58 are respectively cylindrical in shape. The Z-direction shaft 59 has a cylindrical portion 61 and an L-shaped portion 62 provided integrally at a lower end of the cylindrical portion 61, and the housing 45 is secured to a lower end portion of the L-shaped portion 62. The bridging arms 56 and 57 extend in a direction (including the Y direction) perpendicular to the X direction.

On the one side of the median line 30, the above-described supporting means 32 supports the holding means 31 through the bridging arm 56, the X-direction shaft 58, and the Z-direction shaft 59 onto the upright pins 52 and 53 erected uprightly on the model teeth 21 on the one side of the pre-correction dentition model 2 or the post-correction predictive dentition model 3. On the other side of the median line 30, the supporting means 32 supports the holding means 31 through the bridging arm 57, the X-direction shaft 58, and the Z-direction shaft 59 onto the upright pins 54 and 55 erected uprightly on the model teeth 21 on the other side of the pre-correction dentition model 2 or the post-correction predictive dentition model 3.

The position adjusting mechanism 33 includes the pin connector 65 for connecting each of the upright pins 52 and 53 to the bridging arm 56 on the one side of the median line 30 movably along the longitudinal direction of the bridging arm 56 and rotatably in the R1 and R2 directions relative to the bridging arm 56; the pin connector 66 for connecting each of the upright pins 54 and 55 to the bridging arm 57 on the other side of the median line 30 movably and rotatably in the same way as the pin connector 65; an arm connector 67 for connecting the bridging arm 56 to the X-direction shaft 58 on the one side of the median line 30 movably along the longitudinal direction of the bridging arm 56, movably along the longitudinal direction of the X-direction shaft 58, and rotatably in the R1, R3, and R4 directions relative to the X-direction shaft 58; an arm connector 68 for connecting the bridging arm 57 to the X-direction shaft 58 on the other side of the median line 30 movably and rotatably in the same way as the arm connector 67; a shaft connector 69 for connecting the Z-direction shaft 59 to the X-direction shaft 58 movably along the longitudinal direction of the X-direction shaft 58, movably in the Z direction, and rotatably in the R4 and R5 directions relative to the X-direction shaft 58; and an inhibiting member 70 (including inhibiting members 70a to 70f) constituted by a setscrew for releasably inhibiting the aforementioned movement and rotation, respectively, of the upright pins 52 to 55, the bridging arms 56 and 57, the X-direction shaft 58, and the Z-direction shaft 59.

Since the pin connectors 65 and 66 and the arm connectors 67 and 68 are respectively configured in a mutually similar manner, a detailed description will be given hereafter of the pin connector 65 and the arm connector 67, the same reference numerals will be allotted, as required, to the pin connector 66 and the arm connector 68 in the drawings, and a detailed description thereof will be omitted.

The pin connector 65 on the upright pin 52 side includes a connecting body 75; a through hole 76 which is provided in the connecting body 75 and in which the cylindrical bridging arm 56 is inserted; and a connecting portion 78 which is provided on the connecting body 75 and connects to the connecting portion 60 of the upright pin 52 by means of a pin 77. The connecting body 75 is inhibited from moving relative to the bridging arm 56 and rotating about the axis of the bridging arm 56 in the R1 direction by the inhibiting member 70a which is in pressure contact with the bridging arm 56 by means of that connecting body 75. However, when that inhibition by the inhibiting member 70a is released, the connecting body 75, together with the upright pin 52, is adapted to be movable along the longitudinal direction of the bridging arm 56 and rotatable in the direction R1 relative to that bridging arm 56. In addition, the upright pin 52 is inhibited from rotating about the axis of the pin 77 in the direction R2 relative to the pin connector 65 by the inhibiting member 70b which courses the connecting portions 60 and 78 to be in pressure contact with each other. However, when that inhibition by the inhibiting member 70b is released, the upright pin 52 is adapted to be rotatable in the direction R2. It should be noted that since the pin connector 65 on the upright pin 53 side is constructed in the same way as the pin connector 65 on the upright pin 52 side, as for the pin connector 65 on the upright pin 53 side, the same reference numerals will be allotted, as required, and a detailed description thereof will be omitted.

The arm connector 67 includes a pair of connecting members 81 and 82 which are connected to each other rotatably in the R3 direction about an axis extending in the Z direction; a through hole 83 which is provided in the connecting member 81 and in which the cylindrical bridging arm 56 is inserted; and a through hole 84 which is provided in the connecting member 82 and in which the cylindrical X-direction shaft 58 is inserted. The connecting body 81 is inhibited from moving along the longitudinal direction of the bridging arm 56 and rotating in the R1 direction relative to that bridging arm 56 by the inhibiting member 70c which is in pressure contact with the bridging arm 56 by means of that connecting body 81. However, when that inhibition by the inhibiting member 70c is released, the connecting body 81 is adapted to be movable along the longitudinal direction of the bridging arm 56 and rotatable in the direction R1. The connecting body 82 is inhibited from moving along the X-direction shaft 58 and rotating about the axis of the X-direction shaft 58 in the R4 direction relative to that X-direction shaft 58 by the inhibiting member 70d which is in pressure contact with the X-direction shaft 58 by means of that connecting body 82. However, when that inhibition by the inhibiting member 70d is released, the connecting body 82 is adapted to be movable along the X-direction shaft 58 and rotatable in the direction R4. It should be noted that the bridging arm 56 is adapted to be rotated in the R3 direction by the rotation of the connecting member 81 in the R3 direction relative to the connecting member 82.

The shaft connector 69 includes a connecting body 91; a through hole 92 which is provided in the connecting body 91 and in which the cylindrical X-direction shaft 58 is inserted; and a through hole 93 which is provided in the connecting body 91 and in which the cylindrical portion 61 of the cylindrical Z-direction shaft 59 is inserted. The connecting body 91 is inhibited from moving along the X-direction shaft 58 and rotating in the R4 direction relative to that X-direction shaft 58 by the inhibiting member 70e which is in pressure contact with the X-direction shaft 58 by means of that connecting body 91. However, when that inhibition by the inhibiting member 70e is released, the connecting body 91, together with the Z-direction shaft 59, is adapted to be movable along the X-direction shaft 58 and rotatable in the direction R4. In addition, the connecting body 91 is inhibited from moving along the Z-direction shaft 59 and rotating about the axis of the Z-direction shaft 59 in the R5 direction relative to that Z-direction shaft 59 by the inhibiting member 70f which is in pressure contact with the cylindrical portion 61 by means of that connecting body 91. However, when that inhibition by the inhibiting member 70f is released, the connecting body 91 is adapted to be movable along the Z-direction shaft 59 and rotatable in the direction R5.

According to the above-described arranging device 6, the index members 4 and 5 can be respectively arranged at mutually identical reference positions with respect to the respective entireties of the pre-correction dentition model 2 and the post-correction predictive dentition model 3. It should be noted that the arranging device 6 is erected uprightly on the model teeth 21 other than the model teeth 21 corresponding to the teeth to be corrected, as shown in FIG. 2.

The image data generating means 11 has one or two or more imaging devices 101 for imaging the pre-correction dentition model 2 and the post-correction predictive dentition model 3, respectively, under mutually identical conditions, and is adapted to generate the pre-correction dentition image data 9 based on the pre-correction dentition model 2 and the post-correction predictive dentition image data 10 based on the post-correction predictive dentition model 3 by imaging by the imaging device 101. The imaging device 101 may be adapted to image the pre-correction dentition model 2 and the post-correction predictive dentition model 3 by using a CCD, a laser, an X-ray, a CT, a CAT, an MRI, or the like. It should be noted that the pre-correction dentition image data 9 and the post-correction predictive dentition image data 10 are transmitted to the storage means 19 through a signal line 102 in this embodiment. The teeth image data 16 and the index image data 7 are included in the pre-correction dentition image data 9 generated by the image data generating means 11. The teeth image data making up the dentition shape after orthodontics and the index image data 8 are included in the post-correction predictive dentition image data 10 generated by the image data generating means 11. The pre-correction dentition image data 9 and the post-correction predictive dentition image data 10 generated by the image data generating means 11 are constituted by three-dimensional image data. The imaging device 101 is preferably constituted by a laser scanner in the relationship with the projections 26.

The screen display means 14, the overall-position adjusting means 15, the tooth position adjusting means 18, and the storage means 19 are embodied by, for example, a computer including an arithmetic unit such as a CPU, a storage unit such as a memory, a monitor having a CRT, a TFT, or the like, and an operation unit such as a keyboard and a mouse, as well as a program stored in that computer.

As particularly shown in FIGS. 8 to 10, the screen display means 14 has a display screen 111 for screen-displaying the three-dimensional pre-correction dentition image 12 and post-correction predictive dentition image 13 based on the pre-correction dentition image data 9 and the post-correction predictive dentition image data 10 which are supplied from the image data generating means 11 through the storage means 19, and is adapted to perform the screen display as described above and below. In addition, a screen display may be given on the display screen 111 such that the pre-correction dentition image 12 and the post-correction predictive dentition image 13 are superposed on each other, as shown in FIGS. 8 and 9. In addition, a screen display may be given by juxtaposing the pre-correction dentition image 12 and the post-correction predictive dentition image 13, as shown in FIG. 10. In a case where the pre-correction dentition image 12 and the post-correction predictive dentition image 13 to be screen-displayed have been created three-dimensionally, the screen display means 14 is adapted to be able to change the angle of screen-displaying the pre-correction dentition image 12 and the post-correction predictive dentition image 13 on the basis of the operation of the operation unit such as the keyboard and the mouse.

As shown in FIG. 6, the position adjusting means 15 includes an overall-position setting program 115 for setting on the basis of the index image data 7 and 8 the respective overall display positions of the pre-correction dentition image 12 and the post-correction predictive dentition image 13 which are screen-displayed on the display screen 111, as well as an overall-position changing program 116 for changing the overall display position with respect to the post-correction predictive dentition image 13 of the pre-correction dentition image 12 screen-displayed at a position which has been set by the overall-position setting program 115. The overall-position setting program 115 is stored in the storage means 19 so as to be executed on the basis of the operation of the operation unit such as the keyboard and the mouse or so as to be automatically executed in accordance with the storage of the pre-correction dentition image data 9 and the post-correction predictive dentition image data 10 by the storage means 19. The overall-position changing program 116 is stored in the storage means 19 so as to be executed on the basis of the operation of the operation unit such as the keyboard and the mouse.

The overall-position setting program 115 reads out the pre-correction dentition image data 9 and the post-correction predictive dentition image data 10 from the storage means 19, and sets an overall display position in a coordinate system having an X axis, a Y axis, and a Z axis (not shown) of the pre-correction dentition image 12 by using as a reference position the display position of an index image 117 which is to be screen-displayed on the display screen 111 on the basis of the index image data 7 included in the pre-correction dentition image data 9 which has been read out. Also, the overall-position setting program 115 sets an overall display position in a coordinate system having the X axis, the Y axis, and the Z axis (not shown) of the post-correction predictive dentition image 13 by using as a reference position the display position of an index image 118 which is to be screen-displayed on the display screen 111 on the basis of the index image data 8 included in the post-correction predictive dentition image data 10 which has been read out. The overall-position setting program 115 may be adapted to cause display positions in the coordinate systems of the index images 117 and 118 of the pre-correction dentition image 12 and the post-correction predictive dentition image 13 to coincide with each other. In such a case, the respective overall display positions (excluding portions corresponding to teeth images corresponding to the teeth to be corrected) of the pre-correction dentition image 12 and the post-correction predictive dentition image 13 are automatically made to correspond in the computer. The overall-position setting program 115 generates overall-position setting data 121 concerning the coordinate positions of the pre-correction dentition image 12 and the post-correction predictive dentition image 13 after the setting of the overall display positions. The overall-position setting data 121 is stored in the storage means 19.

On the basis of the operation of the operation unit such as the keyboard and the mouse, the overall-position changing program 116 selects the pre-correction dentition image 12 or the post-correction predictive dentition image 13 on the display screen 111, and changes the overall display position in the coordinate system of the selected pre-correction dentition image 12 with respect to the post-correction predictive dentition image 13 or the overall display position in the coordinate system of the selected post-correction predictive dentition image 13 with respect to the pre-correction dentition image 12. The overall-position changing program 116 generates overall-position changing data 122 concerning the coordinate positions of the pre-correction dentition image 12 and the post-correction predictive dentition image 13 after the changing of the overall display positions. The overall-position changing data 122 is stored in the storage means 19.

As shown in FIG. 6, the tooth position adjusting means 18 includes an extraction program 126 serving as an extraction means for extracting from the pre-correction dentition image data 9 the teeth image data 16 corresponding to the tooth to be moved in orthodontics and the teeth image data 125 corresponding to the tooth to be moved in association with the movement of that tooth in orthodontics; a tooth position setting program 128 for setting positions where the teeth images 17 and 127 based on the teeth image data 16 and 125 extracted by the extraction program 126 are to be screen-displayed on the display screen 111, by using the display position of the pre-correction dentition image 12 as a reference; and a tooth position changing program 129 for changing the display positions with respect to the post-correction predictive dentition image 13 of the teeth images 17 and 127 screen-displayed on the display screen 111 at the positions which have been set by the tooth position setting program 128.

The extraction program 126 reads out the pre-correction dentition image data 9 from the storage means 19, and extracts the three-dimensional teeth image data 16 and 125 mainly on the basis of the data on the dentition shape included in the pre-correction dentition image data 9 which has been read out. The extracted teeth image data 16 and 125 are stored in the storage means 19.

The tooth position setting program 128 reads out each of the teeth image data 16 and 125 from the storage means 19, and sets the display position of each of the teeth images 17 and 127 based on each of the teeth image data 16 and 125 which have been read out, mainly in conformity with the dentition shape contained in the pre-correction dentition image 12. The tooth position setting program 128 generates tooth position setting data 130 concerning the respective coordinate positions of the teeth images 17 and 127 after the setting of the display positions. The tooth position setting data 130 is stored in the storage means 19.

On the basis of the operation of the operation unit such as the keyboard and the mouse, the tooth position changing program 129 selects at least either one of the teeth images 17 and 127 on the display screen 111, and changes the display position in the coordinate system with respect to the post-correction predictive dentition image 13 of the selected at least either one of the teeth images 17 and 127. The tooth position changing program 129 generates tooth position changing data 131 concerning the coordinate position of each of the teeth images 17 and 127 after the changing of the display position. The tooth position changing data 131 is stored in the storage means 19.

The storage means 19 which is embodied by a memory (including an HDD or the like) has storage areas for readably storing the overall-position setting program 115, the overall-position changing program 116, the extraction program 126, the tooth position setting program 128, the tooth position changing program 129, the pre-correction dentition image data 9, the post-correction predictive dentition image data 10, the teeth image data 16 and 125, the overall-position setting data 121, the overall-position changing data 122, the tooth position setting data 130, and the tooth position changing data 131, respectively, which are shown particularly in FIGS. 6 and 7.

In the case where the above-described orthodontics assisting system 1 is used, the pre-correction dentition model 2 fabricated on the basis of the patient's dentition shape before orthodontics, the post-correction predictive dentition model 3 having a presumptive predictive dentition shape after orthodontics fabricated by a specialist such as a dentist or a dental engineer; the index members 4 and 5, and the arranging device 6 are prepared first.

Figure 4:
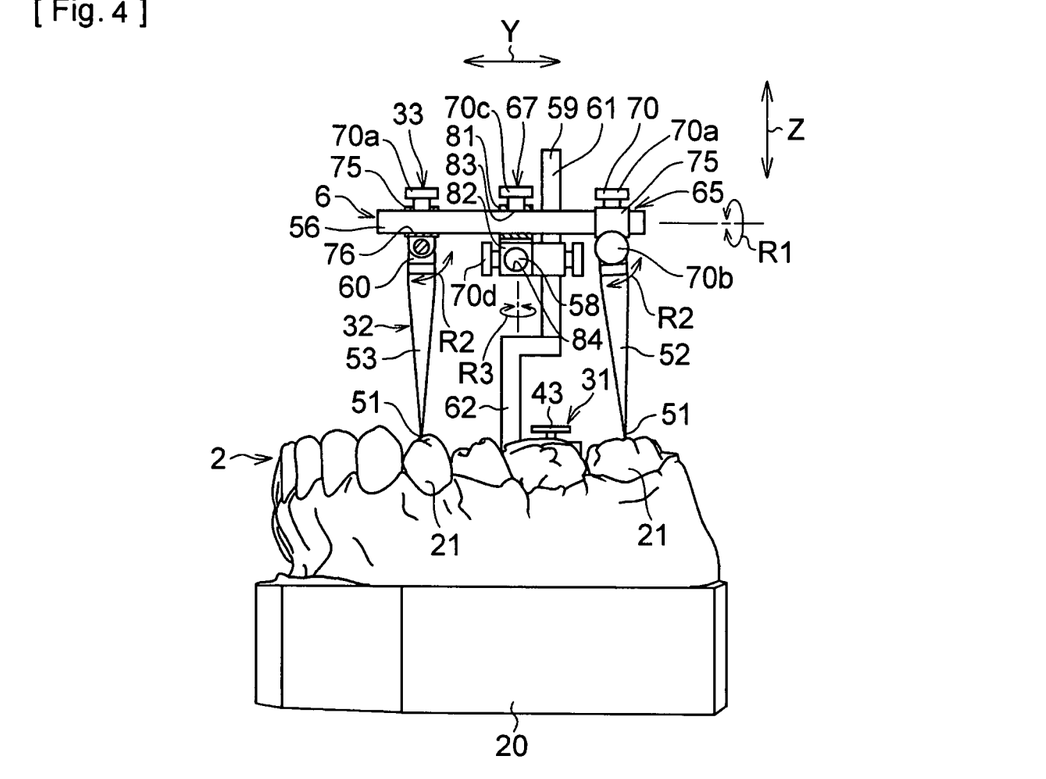
FIG. 4 is an explanatory side elevational view of mainly the arranging device in the embodiment shown in FIG. 1.

Next, the position of each of the upright pins 52 to 55 with respect to the pre-correction dentition model 2 is adjusted so that each of the upright pins 52 to 55 is arranged on the model tooth 21 of the pre-correction dentition model 2 by the position adjusting mechanism 33. Subsequently, each of the upright pins 52 to 55 is erected uprightly on the model tooth 21 of the pre-correction dentition model 2, thereby mounting the arranging device 6 on the pre-correction dentition model 2, as shown in FIGS. 2 to 4. Next, the index member 4 is held by the holding means 31 of the arranging device 6 mounted on the pre-correction dentition model 2, and the position of the held index member 4 with respect to the pre-correction dentition model 2 is adjusted by the position adjusting mechanism 33, thereby arranging the index member 4 with respect to the pre-correction dentition model 2. The plate-like body 25 of the index member 4 arranged by the arranging device 6 is secured to the pre-correction dentition model 2 by means of wax or the like. After the securing of the index member 4, the holding of the index member 4 by the holding means 31 is released, and the arranging device 6 is removed from the pre-correction dentition model 2. As particularly shown in FIG. 2, one or a plurality of model teeth 21 are interposed between the model teeth 21 on which the upright pins 52 and 53 are erected uprightly and between the model teeth 21 on which the upright pins 54 and 55 are erected uprightly, respectively. Next, the arranging device 6 as it is in the state of being adjusted by the position adjusting mechanism 33 at the time of arranging the index member 4 with respect to the pre-correction dentition model 2 is mounted on the post-correction predictive dentition model 3, and after the mounting, the index member 5 is held by the holding means 31. Thus, the index member 5 is arranged with respect to the post-correction predictive dentition model 3 so that the position of the index member 5 with respect to the post-correction predictive dentition model 3 becomes equivalent to the position of the index member 4 with respect to the pre-correction dentition model 2. The plate-like body 25 of the index member 5 arranged by the arranging device 6 is secured to the post-correction predictive dentition model 3 by means of wax or the like. After the securing of the index member 5, the holding of the index member 5 by the holding means 31 is released, and the arranging device 6 is removed from the post-correction predictive dentition model 3. The index members 4 and 5 respectively arranged with respect to the pre-correction dentition model 2 and the post-correction predictive dentition model 3 by the arranging device 6 show the respective overall reference positions of the pre-correction dentition model 2 and the post-correction predictive dentition model 3. It should be noted that the arrangement of the index member 5 with respect to the post-correction predictive dentition model 3 by the arranging device 6 may be carried out earlier than the arrangement of the index member 4 with respect to the pre-correction dentition model 2. In addition, the arranging device 6 may arrange the index member 5 with respect to the post-correction predictive dentition model 3 in a state in which the model teeth 21 have not been cut off from each other and in a state in which the post-correction predictive dentition model 3 has the same dentition shape as that of the pre-correction dentition model 2.

Next, the pre-correction dentition model 2 and the post-correction predictive dentition model 3 provided with the index members 4 and 5 are respectively imaged by the image data generating means 11 to generate the three-dimensional pre-correction dentition image data 9 and post-correction predictive dentition image data 10. The generated pre-correction dentition image data 9 and post-correction predictive dentition image data 10 are stored by the storage means 19.

Next, the overall display position of each of the pre-correction dentition image 12 and the post-correction predictive dentition image 13 to be screen-displayed on the display screen 111 is set by the execution of the overall-position setting program 115. After the execution of the overall-position setting program 115, the pre-correction dentition image 12 and the post-correction predictive dentition image 13 are screen-displayed on the display screen 111 by the screen display means 14. Next, the overall display position with respect to the post-correction predictive dentition image 13 of the pre-correction dentition image 12 screen-displayed at the position set by the overall-position setting program 115 is changed by the execution of the overall-position changing program 116 based on the computer operator's judgment.

Next, the teeth image data 16 corresponding to the tooth to be moved in orthodontics and the teeth image data 125 corresponding to the tooth to be moved in association with the movement of that tooth in orthodontics are extracted from the pre-correction dentition image data 9 by the execution of the extraction program 126, and the positions where the teeth images 17 and 127 based on the extracted teeth image data 16 and 125 are to be screen-displayed on the display screen 111 are set by using the display position of the pre-correction dentition image 12 as a reference by the execution of the tooth position setting program 128. After the execution of the tooth position setting program 128, the teeth images 17 and 127 are screen-displayed on the display screen 111 by the screen display means 14.

Next, the display position with respect to the post-correction predictive dentition image 13 of the teeth image 17 screen-displayed at the position set by the tooth position setting program 128 is changed in steps by the execution of the tooth position changing program 129 based on the computer operator's judgment, so that that teeth image 17 approaches toward a teeth image 137 included in the post-correction predictive dentition image 13. The respective tooth position changing data 131 of the teeth image 17 thus changed in steps are stored in the storage means 19. As for the respective teeth images 127, their display positions can also be changed in the same way as in the case of changing the display position of the teeth image 17. It should be noted that the extraction program 126 may be executed earlier than the overall-position setting program 115.

If the orthodontics assisting system 1 is used as described above, it is possible to generate the various data described above. The above-described various data thus generated are useful in the phased planning of orthodontics and in the fabrication of a dentition model having a dentition shape corresponding to the correction phase of the dentition and an orthodontic mouthpiece which is molded from that dentition model.

According to the orthodontics assisting system 1 in accordance with this embodiment, the orthodontics assisting system 1 is comprised of the index members 4 and 5 which indicate respective overall reference positions of the pre-correction dentition model 2 having a dentition shape before orthodontics and the post-correction predictive dentition model 3 having a predictive dentition shape after orthodontics; the arranging device 6 for arranging the index members 4 and 5 on the pre-correction dentition model 2 and the post-correction predictive dentition model 3, respectively, to cause the index members 4 and 5 to indicate the reference positions, respectively; the image data generating means 11 for generating the pre-correction dentition image data 9 including the index image data 7 based on the index member 4 arranged on the pre-correction dentition model 2 and the post-correction predictive dentition image data 10 including the index image data 8 based on the index member 5 arranged on the post-correction predictive dentition model 3, by imaging the pre-correction dentition model 2 and the post-correction predictive dentition model 3, respectively, with the index members 4 and 5 respectively arranged thereon by the arranging device 6; the screen display means 14 for screen-displaying the pre-correction dentition image 12 and the post-correction predictive dentition image 13 respectively based on the pre-correction dentition image data 9 and the post-correction predictive dentition image data 10 generated by the image data generating means 11; the overall-position adjusting means 15 for adjusting on the basis of the index image data 7 and 8 mutual overall display positions of the pre-correction dentition image 12 and the post-correction predictive dentition image 13 which are screen-displayed by the screen display means 14; and the tooth position adjusting means 18 for extracting the teeth image data 16 and 125 from the pre-correction dentition image data 9 and for adjusting display positions with respect to the post-correction predictive dentition image 13 of the teeth images 17 and 127 based on the extracted teeth image data 16 and 125. Therefore, it is possible to accurately create a desired post-correction predictive dentition image 13 on the basis of the post-correction predictive dentition model 3. Moreover, the mutual positioning of the pre-correction dentition image 12 and the post-correction predictive dentition image 13 can be performed simply and accurately on the basis of the index image data 7 and 8.

According to the orthodontics assisting system 1, since each of the index members 4 and 5 has the plate-like body 25 and the projections 26 provided on the plate-like body 25, by providing these index members 4 and 5 on the pre-correction dentition model 2 and the post-correction predictive dentition model 3, in a case where the pre-correction dentition model 2 and the post-correction predictive dentition model 3 are imaged as image data for use in a computer or the like, the index image data 7 which clearly indicates the reference position of the pre-correction dentition image 12 based on the pre-correction dentition model 2 and the index image data 8 which clearly indicates the reference position of the post-correction predictive dentition image 13 based on the post-correction predictive dentition model 3 can be obtained on the basis of the respective imaged index members 4 and 5. Hence, the mutual positioning of the overall display positions of the pre-correction dentition image 12 based on the pre-correction dentition model 2 and the post-correction predictive dentition image 13 based on the post-correction predictive dentition model 3 can be performed simply and accurately. In addition, according to the orthodontics assisting system 1, since the projections 26 of the index members 4 and 5 are semispherical, the mutual overall display positions of the pre-correction dentition image 12 and the post-correction predictive dentition image 13 can be made to coincide even more simply.

According to the orthodontics assisting system 1, the arranging device 6 includes the holding means 31 for holding the index members 4 and 5; the supporting means 32 which supports the holding means 31 and is mounted on each of the model teeth 21 of the pre-correction dentition model 2 and the post-correction predictive dentition model 3; and the position adjusting mechanism 33 for adjusting the position of the holding means 31 with respect to each of the pre-correction dentition model 2 and the post-correction predictive dentition model 3. Therefore, the index members 4 and 5 can be accurately disposed at arbitrary reference positions with respect to the pre-correction dentition model 2 and the post-correction predictive dentition model 3. Moreover, by similarly adjusting the position of the holding means 31 with respect to each of the pre-correction dentition model 2 and the post-correction predictive dentition model 3 by the position adjusting mechanism 33, the position of the index member 4 with respect to the overall pre-correction dentition model 2 and the position of the index member 5 with respect to the overall post-correction predictive dentition model 3 can be made to accurately coincide with each other. Thus, the mutual overall display positions of the pre-correction dentition image 12 and the post-correction predictive dentition image 13 can be made to more accurately coincide with each other.

According to the orthodontics assisting system 1, the supporting means 32 includes the plurality of upright pins 52 to 55 each having the tip 51 and each adapted at the tip 51 to be abutted against a depression in the occlusal surface 21*a* of the respective model tooth 21 so as to be erected uprightly on that respective model tooth 21. Therefore, the supporting means 32 can be mounted simply and accurately on the respective model teeth 21 of the pre-correction dentition model 2 and the post-correction predictive dentition model 3.

According to the orthodontics assisting system 1, the orthodontics assisting system 1 is further comprised of the storage means 19 for storing the pre-correction dentition image data 9, the post-correction predictive dentition image data 10, the teeth image data 16, and data showing the results of respective position adjustment by the overall-position adjusting means 15 and the tooth position adjusting means 18, respectively. Therefore, if the above-described various data are once created by the orthodontics assisting system 1, those various data can be referred to in an ex-post manner. Thus, it is possible to suitably assist the phased correction planning of orthodontics and the fabrication of orthodontic mouthpieces having various shapes corresponding to such phased correction planning.

It should be noted that the arranging device 6 may include bridging arms, an X-direction shaft, and a Z-direction shaft which are of the telescopic nested type, instead of the bridging arms 56 and 57, the X-direction shaft 58, and the Z-direction shaft 59.

Figure 11:
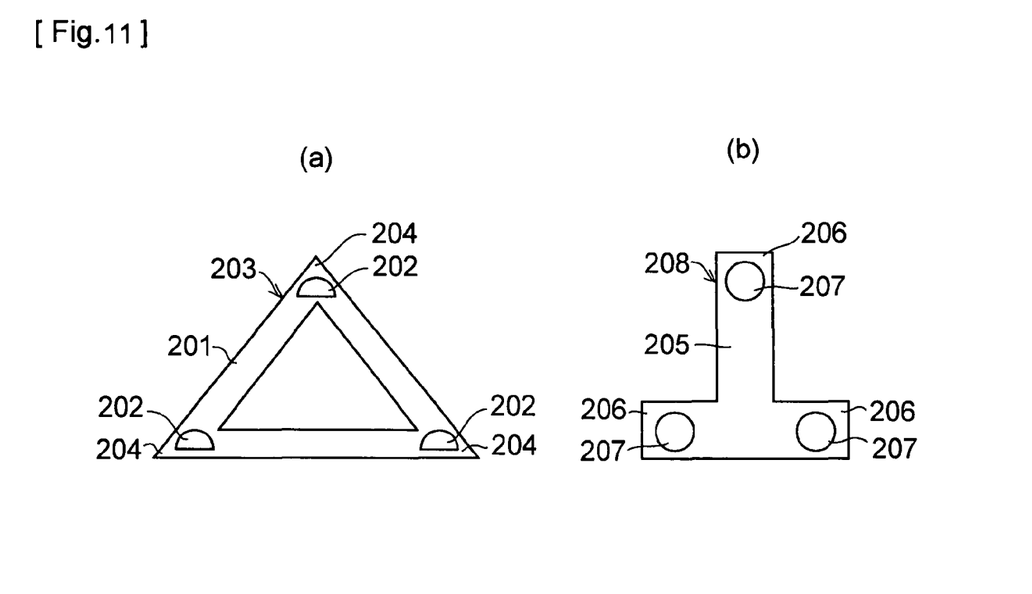

The orthodontics assisting system 1 may include, instead of the index members 4 and 5, an index member 203 having an annular plate-like body 201 and projections 202 which are provided on the plate-like body 201 and are semicircular as viewed from above, as shown in FIG. 11(*a*). Although the annular plate-like body 201 shown in FIG. 11(*a*) has a triangular annular shape, the plate-like body 201 may have, for example, a rectangular annular shape, a polygonal annular shape, a circular annular shape, or the like. Although the projections 202 are respectively provided on three bent portions 204 of the triangular annular plate-like body 201 shown in FIG. 11(*a*), the projections 26 may be provided instead of the projections 202. In addition, the orthodontics assisting system 1 may include, instead of the index members 4 and 5, an index member 208 having a T-shaped plate-like body 205 and projections 207 which are respectively provided on three end portions 206 of the plate-like body 205 and are circular as viewed from above. Although the plate-like body 205 shown in FIG. 11(*b*) has a T-shape, the plate-like body 205 may have, for example, a cruciform shape, in which case four projections 207 may be provided. Although the plate-like body 205 shown in FIG. 11(*b*) is provided with the projections 207, the projections 26 or the projections 202 may be provided thereon instead of the projections 207.

The invention claimed is:

1. An orthodontics assisting system comprising:
a first index member which indicates reference positions of a pre-correction dentition model having a dentition shape before orthodontics; a second index member which indicates reference positions of a post-correction predictive dentition model having a predictive dentition shape after orthodontics;
an arranging device for arranging said first and second index members on the pre-correction dentition model and the post-correction predictive dentition model, respectively, to cause said first and second index members to indicate the reference positions, respectively;
image data generating means for generating pre-correction dentition image data including first index image data based on said first index member arranged on the pre-correction dentition model and post-correction predictive dentition image data including second index image data based on said second index member arranged on the post-correction predictive dentition model, by imaging the pre-correction dentition model and the post-correction predictive dentition model, respectively, with said first and second index members respectively arranged thereon by said arranging device;
screen display means for screen-displaying a pre-correction dentition image and a post-correction predictive dentition image respectively based on the pre-correction dentition image data and the post-correction predictive dentition image data generated by said image data generating means; position adjusting means for adjusting on the basis of the first and second index image data mutual overall display positions of the pre-correction dentition image and the post-correction predictive dentition image which are screen-displayed by said screen display means; and
tooth position adjusting means for extracting teeth image data from the pre-correction dentition image data and for adjusting display positions with respect to the post-correction predictive dentition image of teeth images based on the extracted teeth image data,
said arranging device including holding means for holding the index members; supporting means which supports said holding means and is mounted model teeth of the pre-correction dentition model and the post-correction predictive dentition model; and a position adjusting mechanism for adjusting the position of said holding means with respect to each of the pre-correction dentition model and the post-correction predictive dentition model.

2. The orthodontics assisting system according to claim 1, wherein said first and second index members have a plate-like body and a projection provided on the plate-like body.

3. The orthodontics assisting system according to claim 2, wherein the projection of said first and second index members are semispherical.

4. The orthodontics assisting system according to claim 1, wherein said supporting means includes a plurality of upright pins each having a tip and each adapted at the tip to be abutted against a depression in an occlusal surface of the respective model tooth so as to be erected uprightly on that respective model tooth.

5. The orthodontics assisting system according to claim 1, further comprising:
storage means for storing the pre-correction dentition image data, the post-correction predictive dentition image data, the teeth image data, and data showing results of respective position adjustment by said position adjusting means and said tooth position adjusting means, respectively.

6. An orthodontics assisting system comprising:
a first index member which indicates reference positions of a pre-correction dentition model having a dentition shape before orthodontics; a second index member which indicates reference positions of a post-correction predictive dentition model having a predictive dentition shape after orthodontics;
an arranging device to arrange said first and second index members on the pre-correction dentition model and the post-correction predictive dentition model, respectively, to cause said first and second index members to indicate the reference positions, respectively;
an image data generating device to generate pre-correction dentition image data including first index image data based on said first index member arranged on the pre-correction dentition model and post-correction predictive dentition image data including second index image data based on said second index member arranged on the post-correction predictive dentition model, by imaging the pre-correction dentition model and the post-correction predictive dentition model respectively, with said first and second index members respectively arranged thereon by said arranging device;
a screen display device to screen-display a pre-correction dentition image and a post-correction predictive dentition image, respectively, based on the pre-correction dentition image data and the post-correction predictive dentition image data generated by said image data generating device;
a position adjusting device to adjust on the basis of the first and second index image data mutual overall display positions of the pre-correction dentition image and the post-correction predictive dentition image which are screen-displayed by said screen display device; and a tooth position adjusting device to extract teeth image data from the pre-correction dentition image data and to adjust display positions with respect to the post-correction predictive dentition image of teeth images based on the extracted teeth image data, said arranging device including a holding device to hold the index members;

a supporting device which supports said holding device and is mounted on each of the model teeth of the pre-correction dentition model and the post-correction predictive dentition model; and a position adjusting mechanism to adjust the position of said holding device with respect to each of the pre-correction dentition model and the post-correction predictive dentition model.

7. The orthodontics assisting system according to claim 6, wherein said first and second index members have a plate-like body and a projection provided on the plate-like body.

8. The orthodontics assisting system according to claim 7, wherein the projection of said first and second index members are semispherical.

9. The orthodontics assisting system according to claim 6, wherein said supporting device includes a plurality of upright pins each having a tip and each adapted at the tip to be abutted against a depression in an occlusal surface of the respective model tooth so as to be erected uprightly on that respective model tooth.

10. The orthodontics assisting system according to claim 6, further comprising:

a storage device to store the pre-correction dentition image data, the post-correction predictive dentition image data, the teeth image data, and data showing results of respective position adjustment by said position adjusting mechanism and said tooth position adjusting device, respectively.

* * * * *